US00PP32132P2

(12) United States Plant Patent
Hansen

(10) Patent No.: US PP32,132 P2
(45) Date of Patent: Aug. 25, 2020

(54) ***BERGENIA* PLANT NAMED 'MISS PIGGY'**

(50) Latin Name: ***Bergenia crassifolia* (L.) Fritsch; [*Bergenia cordifolia* (Haw.) Sternb.]**
Varietal Denomination: Miss Piggy

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/602,727

(22) Filed: Nov. 26, 2019

(51) Int. Cl.
*A01H 6/80* (2018.01)
*A01H 5/02* (2018.01)

(52) U.S. Cl.
USPC ..... Plt./409

(58) Field of Classification Search
USPC ..... Plt./409
CPC ..... A01H 6/80; A01H 5/02
See application file for complete search history.

*Primary Examiner* — Annette H Para

(57) ABSTRACT

A new and distinct Heartleaf *Bergenia* plant, *Bergenia* plant named 'Miss Piggy' with low, spreading, mounded habit, large, densely-arranged, deep-green, glossy, obovate, evergreen and pink campanulate flowers on heavily-branched, large panicles over a four-week period beginning in early spring. The flowers hold up well in the garden as a landscape plant or as cut flowers. The new plant has a medium growth rate and is naturally resistant to deer and rabbit foraging.

1 Drawing Sheet

Botanical designation: *Bergenia crassifolia* (L.) Fritsch; [*Bergenia cordifolia* (Haw.) Sternb.].

Cultivar denomination: 'Miss Piggy'.

STATEMENT REGARDING PRIOR DISCLOSURES UNDER 37 CFR 1.77(b)(6)

The original disclosure of the claimed plant was made by Walters Gardens, Inc. on Dec. 1, 2018 when the claimed plant was displayed as a photograph with a non-enabling brief description in a website maintained by Walters Gardens, Inc., who obtained the plant and all information relating thereto, from the inventor. No plants of *Bergenia* 'Miss Piggy' have been sold, in this country or anywhere in the world as of the filing date of this application, nor has any disclosure of the new plant been made, more than one year prior the filing date of this application, and such disclosure within one year was either derived directly or indirectly from the inventor.

BACKGROUND OF THE PLANT

The present invention relates to the new and distinct Heartleaf *Bergenia* herein also referred to as *Bergenia* 'Miss Piggy', by the cultivar name, 'Miss Piggy', or as the new plant. The new plant was hybridized by the inventor on Apr. 3, 2013 from a self-pollinated plant of *Bergenia* 'Sakura' (not patented), in a greenhouse of a wholesale perennial grower in Zeeland, Mich. The single seedling represented by 'Miss Piggy' was selected from a group of seedlings by the inventor, isolated and compared in subsequent years to other *Bergenia* and subsequently found to be different from all cultivars known to the discoverer and eventually given the breeder code 13-9-31.

Asexual propagation at the same nursery in Zeeland, Mich., USA initially by division and later by shoot tip sterile tissue culture has shown 'Miss Piggy' to be stable and reproduce true to type in successive generations since late summer of 2015.

SUMMARY OF THE PLANT

*Bergenia* 'Miss Piggy' has not been observed in all possible environmental conditions. The phenotype may vary slightly with changes in environments such as light intensity, fertility, water availability, etc. without, however any variation in genotype.

*Bergenia* 'Miss Piggy' is distinct from all cultivars known to the inventor in the following traits:

1. Low, spreading, mounded habit;
2. Large, densely-arranged, deep-green, glossy, obovate, evergreen foliage;
3. Heavily-branched, large panicle with pink bell-shaped flowers over a long period in spring holds up well in the garden or as a cut flower;
4. Medium growth rate;
5. Naturally resistant to deer and rabbit.

Plants of *Bergenia* 'Miss Piggy' are most similar to 'Flirt' U.S. Plant Pat. No. 26,355 and 'Pink Dragon' (not patented). 'Miss Piggy' has larger and broader foliage and is taller in habit of both foliage and flower than both 'Flirt' and 'Pink Dragon'. 'Flirt' has smaller inflorescences and deeper pink flowers over a shorter period of time. 'Pink Dragon' has slightly deeper pink flowers on smaller inflorescences. Compared to 'Sakura', 'Miss Piggy' has more consistent pink flower color, a larger canopy of foliage, and broader, more substantial leaves.

BRIEF DESCRIPTION OF THE DRAWINGS

The color drawings illustrate the overall characteristics of *Bergenia* 'Miss Piggy' as a four-year-old plant. The colors are as true as reasonably possible given the technology available. The color values may vary slightly depending on light intensity and quality.

DETAILED BOTANICAL DESCRIPTION

Figure 1:
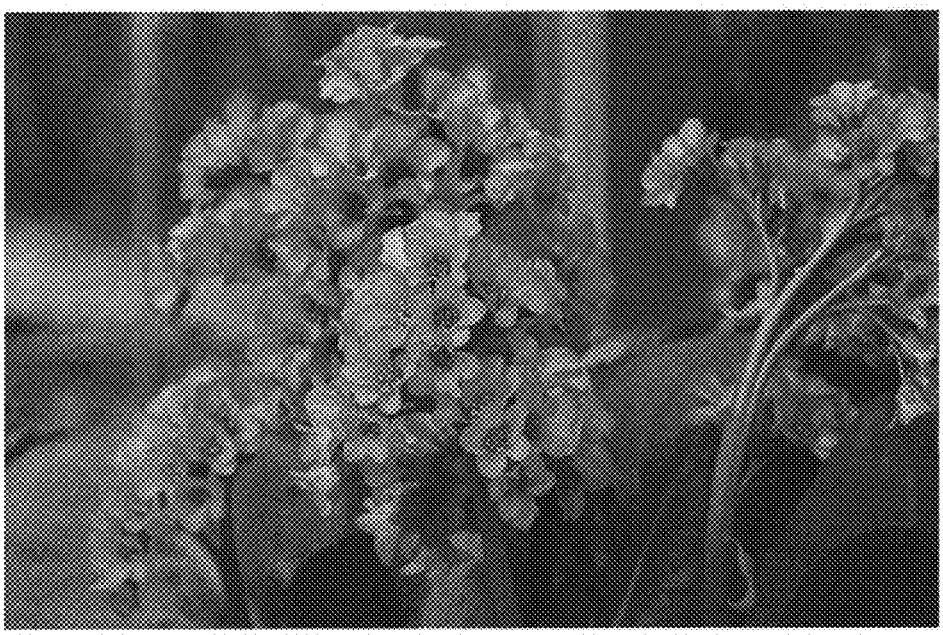
FIG. 1 shows a close-up of the flowers of the new plant.
Figure 2:
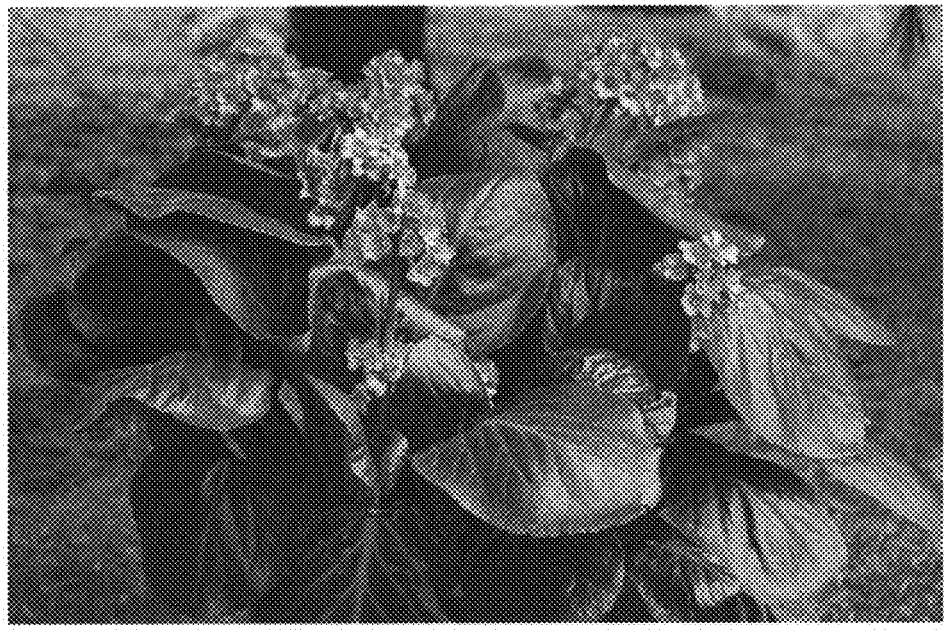
FIG. 2 shows the new plant in a landscape environment.

The following description is based on two-year-old plants growing in a partially-shaded greenhouse in Zeeland, Mich., USA. Except for ordinary dictionary color usage, color references are according to The Royal Horticultural Society Colour Chart, 2015 edition. The new plant has not been observed in all possible growing conditions and may vary in phenotypic characteristics based on water availability, light conditions, fertilizer, temperatures, etc. without varying in genotypic characteristics.

Parentage: Female or seed parent 'Sakura'; male or pollen parent 'Sakura';

Asexual propagation: Division of tissue culture plants, about 21 days to initiate roots; time to finish 25 mm plugs in a one-gallon container about 3 months; moderate growth rate;

Plant habit: Low, spreading, mounded, herbaceous, evergreen, winter-hardy, perennial mound; with heavily branched flower stems; with about 19 shoots per plant; shoots to about 6.0 cm long and about 3.8 cm diameter;

Plant size: Foliage up to about 70.0 cm wide and about 41.0 cm tall; flowering to about 45.0 cm tall and about 45.0 cm tall;

Leaves: Alternate; simple; coriaceous; obovate to ovate; adaxial and abaxial surface lustrous; rounded apex; cuneate base; margin irregularly dentate; up to 24.0 cm long and 17.0 cm wide, average about 18.5 cm long and about 15.0 cm wide;

Leaf color: Young expanding leaves adaxial nearest blend of RHS 137C and RHS 144A and abaxial nearest RHS 146C; mature leaves adaxial nearest RHS 139A, abaxial nearest RHS 146B; winter color developing variable moderate to strong blush of between RHS 53A and RHS 53B;

Veins: Pinnate;

Vein color: Adaxial basally blend between RHS 144A and RHS 143C, distally becoming RHS 139A, abaxial basally nearest blend between RHS 143C and RHS 144A, distally becoming nearest RHS 146B;

Inflorescence peduncle: Panicle; about 12 per plant; about 45.0 cm long and 10.0 mm diameter at base; cylindrical; sparsely minutely hispidulous;

Peduncle color: Variable, proximal portion nearest blend of RHS 145A and RHS 146D, distally nearest RHS 146D with minor to moderate blushing of nearest RHS 178B;

Flower: Single; perfect; campanulate; on terminal branches; about 37.0 mm across, about 23.0 mm long; attitude outright to slightly drooping;

Inflorescence fragrance: Not detected;

Calyx: Campanulate; to about 12.0 mm wide and 12.0 mm long;

Sepals: Five; ovate; broadly acute apex; truncate base; margin entire; glabrous and lustrous adaxial; abaxial micro-glandular, slightly lustrous; about 11.5 mm long and about 5.0 mm wide;

Sepal color: Variable, adaxial nearest RHS 146B with thin marginal rim nearest RHS 184B, abaxial nearest RHS 178B; other sepals adaxial nearest RHS 145A with slight blush of nearest RHS 184B and abaxial blend between RHS 145A and RHS 146D;

Flowering period: Beginning early spring, for about 4 weeks; producing up to 85 flowers per branched stem and 23 flowers per branch;

Flower longevity: 7 to 10 days;

Flower buds one day prior to opening: Oblong, acute apex, about 13.0 mm long and 8.0 mm diameter;

Flower bud color one day prior to opening: Exposed petals nearest RHS 68A, sepals nearest RHS 176B;

Pedicel: Cylindrical; glaucous; lustrous; average about 12.0 mm long and 2.0 mm diameter;

Pedicel color: Variable; nearest RHS 146D with blush of nearest RHS 181A to nearly solid RHS 181A to solid RHS N45A;

Petals: Typically five in single whorl, rarely six; obovate; rounded apex; attenuate to cuneate base; margin entire; glabrous adaxial abaxial; imbricate near longitudinal middle; about 23.0 mm long and 15.0 mm wide near middle;

Petal color: Variable; when initially open adaxial nearest RHS NN74B around the 0.5 mm margin, proximal midrib nearest RHS NN155D with the remainder transitioning to nearest a blend of RHS NN74C to RHS N74C, abaxial 0.5 mm wide margin nearest RHS NN74B, midrib nearest RHS NN155D with remainder transitioning to nearest blend between RHS NN74C and RHS N74C; mature adaxial or abaxial nearest RHS N74D with basal midribs nearest RHS NN155D; before dehiscing adaxial and abaxial nearest a blend between RHS 76C and RHS 77D with basal midribs nearest RHS 64C;

Androecium: Typically ten; about 12.0 mm long;

*Filament.*—About 10.0 mm long and 0.7 mm diameter; color nearest RHS 155C.

*Anther.*—Ellipsoidal; basifixed; longitudinal; about 2.5 mm long and 1.0 mm across; color nearest RHS 4D.

*Pollen.*—Abundant; color nearest RHS 13C.

Gynoecium: Double; about 15.0 mm long;

*Ovary.*—Partly inferior.

*Style.*—Cylindrical; about 9.0 mm long and 3.5 mm diameter above ovary; color nearest RHS 146D.

*Stigma.*—Loosely lobed; about 3.0 mm wide, 1.0 mm across and 1.0 mm tall; color nearest initially nearest RHS 145B, at flower maturity nearest RHS 187B.

Seed: Ellipsoidal; acute apex and rounded base; surface glabrous; about 2.0 mm long and 0.5 mm across center; color nearest RHS 200B; *Bergenia* 'Miss Piggy' is tolerant of winter temperatures from USDA hardiness at least from zones 4 to 8. The new plant grows best with good drainage and adequate moisture. It is not known to be tolerant of diseases and pest that are common to other Heartleaf *Bergenia* cultivars.

I claim:

1. A new and distinct cultivar of *Bergenia* plant named 'Miss Piggy' as described and illustrated.

* * * * *